(12) United States Patent
Ringold

(10) Patent No.: US 8,728,751 B2
(45) Date of Patent: May 20, 2014

(54) SYSTEM AND METHOD FOR DIAGNOSING LYMPHOMA IN CATS

(75) Inventor: Randy Ringold, West Hills, CA (US)

(73) Assignee: Veterinary Diagnostics Institute, Inc., Simi Valley, CA (US)

( * ) Notice: Subject to any disclaimer, the term of this patent is extended or adjusted under 35 U.S.C. 154(b) by 415 days.

(21) Appl. No.: 13/084,807

(22) Filed: Apr. 12, 2011

(65) Prior Publication Data
US 2012/0264151 A1  Oct. 18, 2012

(51) Int. Cl.
*C12Q 1/50* (2006.01)
(52) U.S. Cl.
USPC ............................. 435/17; 435/7.72
(58) Field of Classification Search
USPC .................................. 435/17, 7.72
See application file for complete search history.

(56) References Cited

U.S. PATENT DOCUMENTS

2009/0111135 A1  4/2009  Ringold et al.

OTHER PUBLICATIONS

Plasma Thymidine kinase activity in dogs with lymphoma and leukemia. Nakamura et al. J. Vet. Med. Sci. 59(10): 957-960, 1997.

*Primary Examiner* — Bin Shen
(74) *Attorney, Agent, or Firm* — Karim Lagobi

(57) ABSTRACT

The invention provides a method and a system for diagnosing lymphoma in cats. The system allows a care giver to measure the enzymatic activity of thymidine kinase in a blood sample. The invention teaches that when the enzymatic activity of thymidine kinase in the blood stream of a cat is above 15.5 Units per liter, the cat has a high probability of having lymphoma. The invention allows for initial diagnosis, follow up after treatment for lymphoma and/or monitoring for example in breeds that prone to have lymphoma.

9 Claims, 4 Drawing Sheets

SYSTEM AND METHOD FOR DIAGNOSING LYMPHOMA IN CATS

FIELD OF THE INVENTION

The invention relates to diagnosing lymphoma in cats; more specifically the invention provides a method and system for diagnosing the presence of lymphoma cancerous cells through the measurement of thymidine kinase enzymatic activity in the blood.

BACKGROUND OF THE INVENTION

Lymphocytes are found in various organs of the body in vertebrates, and are part of the immune system. They attack foreign bodies, and in instances of cells that have been infected with a virus, they attack the body's own cells. But, Lymphocytes can become cancerous and cause a cancer known both as Lymphoma or Lymphosarcoma. Since lymphocytes are found in multiple organs, cancerous lymphocytes may develop a tumor in a variety of organs.

In cats, where lymphoma is a common cancer, diagnosing Lymphoma is problematic, due to the fact that the symptoms may vary depending on the affected organ. For instance, the symptoms that develop as a result of Lymphoma in cats such as loss of appetite, weight loss, vomiting and diarrhea, that are also typically indicative of Inflammatory Bowel Disease (IBD). Relying on these symptoms alone may lead to a miss-diagnosis of IBD, when the real underlying disease is Lymphoma.

Consequently, mistakenly diagnosing IBD instead of Lymphoma may lead to treatments that typically involve using steroids (e.g., Prednisone). The steroid treatment, although appears to relieve the symptoms, promotes the progression of cancerous cells, thus complicating the detection of the true cause of the symptoms (i.e., lymphoma), and later treatment of lymphoma.

The existing approach to detecting lymphoma is through a histological investigation, which involves a biopsy i.e., a surgical procedure to collect tissue, and testing to detect the presence of cancerous cells. A laboratory test may be, however, too costly, and may only be carried out at a late stage of the diagnosis elimination process i.e. after other conditions have been ruled out. As consequence, the delay caused by going through the diagnostic stages until a trial diagnosis of lymphoma is conducted, may be detrimental to the success rate of the treatment of the cancer once it has been established.

Therefore, what is needed is a method and system that allows a practitioner to detect, with a high probability, the presence of lymphoma in cats in order to guide further diagnoses of the disease, thus reducing the cost through avoidance of conducting multiple diagnoses, preventing miss-diagnoses which may lead to treatments, which may worsen the cancerous condition, and allow for an early diagnosis of lymphoma, before further growth and/or formation of metastases, which may be highly beneficial to the success rate of the cancer treatment once cancer has been established.

SUMMARY OF THE INVENTION

The invention discloses a method and system that enables a care giver to diagnose the presence of lymphoma in cats. In cases when symptoms may point to inflammatory bowel disease (IBD), a diagnosis conducted in accordance to the teachings of the invention would allow the practitioner to determine whether the symptoms are due to inflammatory bowel disease or to lymphoma.

The invention relies on the measurement of thymidine kinase in the blood circulation to determine whether a cat has a high probability of having lymphoma. A higher-than-normal presence of thymidine kinase in the blood is indicative of the presence of lymphoma, in accordance with the teachings of the invention.

The invention teaches to measure the enzymatic activity of thymidine kinase, and provides a level of enzymatic activity of thymidine kinase in the the blood at/or above which the practitioner may suspect a high probability of presence of lymphoma.

The method and system disclosed herein allow a practitioner to detect a probability of presence of lymphoma in cats in order to guide further diagnoses of the disease. Thus the invention provides means to reduce cost by the avoidance of conducting multiple diagnoses, preventing miss-diagnoses which may lead to treatments that may worsen the cancerous condition, and allow for an early diagnosis of lymphoma, before further growth and/or formation of metastases, which may be highly beneficial to the success rate of the cancer treatment once cancer has been established.

The method and system of the invention may also be used for routine monitoring of suspected cases, such as in some breeds that are prone to developing lymphoma, and/or provide routine testing following a treatment for lymphoma. The method and system of the invention may also be useful for providing a prognosis for expected survival based on the level of presence of thymidine kinase in the blood stream.

DETAILED DESCRIPTION OF THE INVENTION

Figure 1:
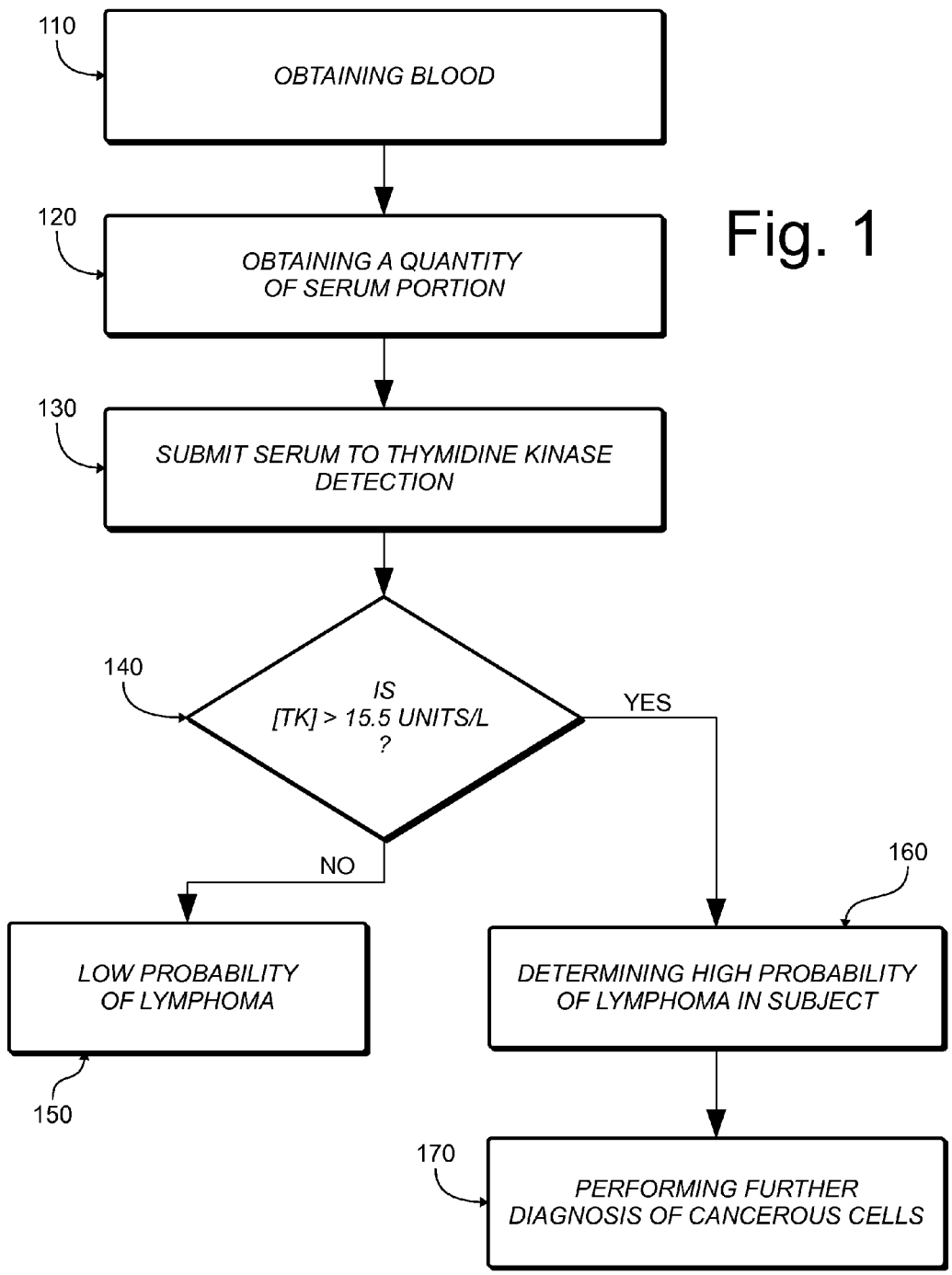
FIG. 1 is a flowchart diagram showing method steps carried out to diagnose lymphoma in cats, in accordance with an embodiment of the invention.

The invention provides a method and system that allow a practitioner to detect a high probability of presence of lymphoma in cats. In order to guide further diagnoses of the disease, thus reducing the cost by the avoidance of conducting multiple diagnoses, preventing miss-diagnoses which may lead to treatments that may worsen the cancerous condition, and allow for an early diagnosis of lymphoma, before further growth and/or formation of metastases, which may be highly beneficial to the success rate of the cancer treatment once cancer has been established.

In the following description, numerous specific details are set forth to provide a more thorough description of the invention. It will be apparent, however, to one skilled in the pertinent art, that the invention may be practiced without these specific details. In other instances, well known features, and procedures, have not been described in detail so as not to obscure the invention. The claims following this description are what define the metes and bounds of the invention.

Thymidine kinase ("TK") is an enzyme that phosphorylates thymidine, one of the building blocks of Deoxyribo-Nucleic Acid (DNA). TK is a salvage enzyme that is present in cells preparing to undergo cell division, a stage to which it is also referred as mitosis. Once TK is no longer needed, it is broken down through a special cellular mechanism, although, a portion of TK escapes to the blood stream. Therefore, in healthy subjects, the amounts of TK found in the blood stream are very low. In the presence of a tumor, however, the amount of TK released in circulation is relatively high, which is likely due to the disruption of cell membranes of dead (or dying) cancerous cells.

The invention utilizes the presence of TK in amounts higher than levels found in the blood stream of healthy subjects to serve as an indicator of the presence of malignant cell proliferation. Furthermore, the level of TK may also be correlated with the aggressiveness of the tumor.

Thymidine kinase is a protein, it may be isolated and measured in the the blood using any of the available methods for isolating and measuring proteins. However, the specific enzymatic property of TK provides a method of measuring the amount of TK present in a fluid by characterizing its enzymatic activity in a controlled biochemical reaction.

In accordance with embodiments of the invention, enzymatic characterization is carried out by providing the initial substrates for the biochemical reaction in a solution that is added to a solution containing TK. The result of the biochemical reaction is selected to be a product that can be measured in the solution either directly or following one or more treatments, such as coloring and/or forming a complex with a marker such as an antibody. The activity of an enzyme is characterized by the amount of substrate consumed through the enzymatic reaction per unit of time under defined conditions.

While other methods for measuring the concentration of TK may be used by embodiments of the invention, one embodiment of the invention utilizes the measurement of the enzymatic activity of TK in order to determine a level of activity that enables a practitioner to cost-effectively determine a probability that a cat carries lymphoma.

Tests have been conducted using the teachings of the invention in order to determine a level of TK in the blood stream that may be used as a marker of the presence of lymphoma. Blood serum was collected from two (2) groups of cats. Both groups showed symptoms that included one or more of loss of appetite, weight loss, vomiting and diarrhea, which may lead a practitioner to diagnose the affected cats with inflammatory bowel disease (IBD). However, the groups in the test were properly diagnosed for lymphoma through other means, such as histological laboratory tests. One group was labeled as a lymphoma-positive and the other as a lymphoma-negative.

Using the method of the invention, TK serum was collected from each individual, and TK activity measured. The results showed most individuals that has been shown to be lymphoma-positive had a serum level of TK that was 15.5 Units/L or higher. The lymphoma-negative subjects, on the other hand, had a level of TK in the serum that was mostly below 15.5 Units/L. At the latter level, statistical analysis showed a significant difference between the two groups. Thus, the invention provides a threshold level that points to a probability that a subject under diagnosis may carry lymphoma based on the result of testing TK activity in the serum of that subject.

FIG. 1 is a flowchart diagram showing method steps carried out to diagnose lymphoma in cats, in accordance with an embodiment of the invention. At step 110, blood is collected from a cat. The latter step is carried out in accordance with standard practices for collecting blood from a cat or any other animal.

The blood sample may be submitted to extraction of the serum portion, at step 120. The latter step may involve using a centrifuge to separate blood cells from serum. However, an embodiment of the invention may utilize any available method to obtain a portion of the collected blood measurably containing thymidine kinase. The portion of blood to be submitted to the detection test may also contain thymidine kinase isoenzymes. Isoenzymes are enzymes that may vary in their structure, but perform similar enzymatic function.

A method in accordance with the invention may utilize a portion of serum of at least 150 µl, obtained by separating the serum portion of the blood sample previously obtained. The amount of serum utilized may vary depending on the method implementing the invention, provided that the amount of serum is measured accurately for the purpose of accurately calculating the level of enzymatic activity per unit of blood volume.

At step 130, a predetermined quantity of extracted blood is submitted to a test that measures the concentration of TK in the blood. For example, the test may involve measuring the enzymatic activity of TK. Once the concentration of TK is measured, at step 140 a test of the concentration is compared with a predefined threshold (e.g., 15.5 Units per liter) that indicates whether the subject has a high probability of having lymphoma. At step 150, a lower amount of TK is detected, and the diagnosis points to an absence of lymphoma.

At step 160, a determination is made that a cat has a high probability of having lymphoma based on the an amount of TK higher the set threshold. Then at step 170, further tests are carried out to further diagnose lymphoma in the affected cat.

Figure 2:
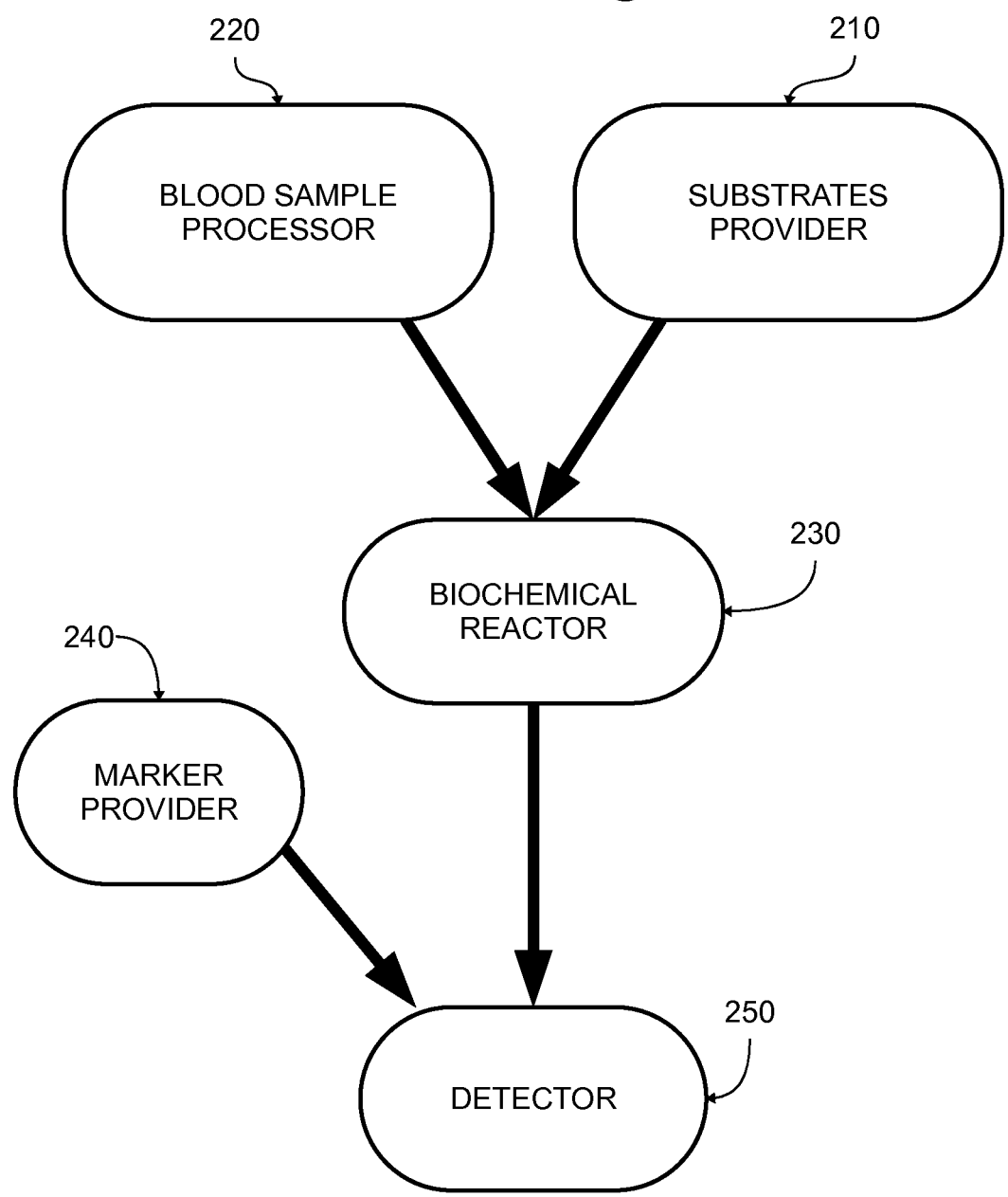
FIG. 2 is a block diagram representing components of a system for diagnosing lymphoma in cats in accordance with an embodiment of the invention.

FIG. 2 is a block diagram representing components of a system for diagnosing lymphoma in cats in accordance with an embodiment of the invention. The latter system utilizes the enzymatic property of TK to detect the amount of TK in a blood sample. However, the invention may utilize one or more methods for detecting the amount of TK present the blood using a system that implements the components represented in FIG. 2.

Block 210 represent a subsystem that prepares the compounds used as a substrate for the enzymatic reaction which TK will be catalyzing. The substrates comprise a thymidine provider and a phosphate donor. The latter substances are selected with the goal that a chemical reaction (e.g., phosphorylation) occurs specifically due to the presence and action of TK present in blood sample.

For example, the thymidine provider may be 3'-derivative of thymidine. The phosphate donor may be a nucleoside triphosphate suitable to transfer a phosphate group to a substrate such as adenosine triposphate (ATP) or cytidine triphosphate (CTP).

Block 220 represents a subsystem used to prepare blood samples, or samples of a portion thereof. For example, the subsystem may include one or more centrifuges, electrophoresis systems, filtering systems, cooling and heating systems and any other system that may be utilized to separate a portion of the blood, and preserve samples for immediate and/or delayed use. The subsystem represented by block 220, comprises a sample transport system that enables a practitioner to prepare blood samples in one location and transport the samples to another location for testing, while preserving the physical, chemical and biochemical properties of the samples.

Block 230 represents a subsystem where the biochemical reactions take place by mixing the substrates and the blood sample. Subsystem of block 230 may include a system of precision pipettes, test tubes, automated mechanisms for collecting aliquots and any other available machine for carrying out a biochemical reaction in order to measure the amount of a protein, such as an enzyme, and/or characterize a level of its activity.

In an embodiment of the invention, subsystem 230 is a machine equipped with a pipette system capable of carrying out a batch of reactions in parallel. The system mixes a quantity of blood sample with a quantity of thymidine compound and phosphate donor in order to allow the TK present in the blood to catalyze a biochemical reaction. The latter is a phosphorylation reaction of a thymidine derivative.

Block 240 represents a marker provider. A marker may utilize any of the physical properties that allow for detecting the quantity of a substance. For example, a marker may carry a luminescent compound, that can be detected and the concentration of which measured by measuring a light emitted by the compound. In other instances, the marker may be fluorescent, carry a radioactive isotope, magnetized beads or any other physical property that facilitates processing of the reaction solution and/or detection of compounds. Furthermore, the marker is typically manufactured to attach to a specific molecular target, such as the product of the biochemical reaction, and form a molecular complex that can be specifically measured. The means for attaching the marker to the product typically utilize an antibody that is specifically manufactured to attach to the target reaction product.

Block 250 represents one or more components of the system that allow for measuring a product. The latter subsystem may be an integral part of the reactor 230, and may involve automated mechanisms for washing a product, one or more compounds for increasing the sensitivity of the detection and any other component of a system that facilitates measurement of the reaction product. Block 250, also represents one or more machines for detecting the reaction product. For example, block 250 may include one or more spectrometers, immunoassay measurement systems and any other necessary tool for measuring the amount of the reaction product.

The following is a test setup for diagnosing lymphoma in cats using the enzymatic activity of TK as a means to measure the amount of TK present in a sample of blood. For each sample, approximately 500 µl of serum was provided. Each sample was labeled with a database code for blind testing and patient identification. The control group included cats that showed symptoms of IBD. From each cat approximately 3 ml whole blood from a peripheral vein was extracted into a red-top tube. For each sample serum were separated from the cells within 60 minutes and the samples were then frozen immediately.

The blood samples were then defrosted and analyzed using the thymidine kinase assay made by DiaSorin S.P.A., Italy, and sold under the Trademark LIAISON®. The analysis included reacting each sample with a substrate having 3'-derivative of thymidine in the presence of a phosphate donor and a buffer system. The phosphate donor was a nucleoside triphosphate suitable to transfer a phosphate group to a substrate such as adenosine triposphate (ATP) or cytidine triphosphate (CTP). The buffer system included 10-100 mM HEPES or Tris with pH ranging from 6.8-8.0, 1-30 mM DTE, 0.2-8 mM ATP and $MgCl_2$ at a concentration of at least two times the concentration of ATP. The substrate contained 3'-derivative of thymidine. A more detailed discussion of the assay can be found in patent application publication No. 2006/0035295 A1 to Oehrvik et al., the specification of which is incorporated herein in its entirety by reference for background information.

The LIAISON®™ TK assay procedure includes a two-step, competitive chemiluminescence immunoassay (CLIA) for quantitative determination of TK in serum and EDTA plasma. The assay utilizes an initial enzymatic reaction in which TK in the sample converts AZT (3'-azido-3'-deoxythymidine) to AZTMP (3'-azido-3'-deoxythymidine mono phosphate). This is followed by a competitive immunoassay for the quantitative determination of AZTMP. The amount of AZT converted to AZTMP is a measure of the amount of TK present in the sample.

In some tests, 50 µl of sample was incubated with 100 µl of Assay Buffer 1, 20 µl of Assay Buffer 2, and 20 µl of paramagnetic particles coated with anti-AZTMP polyclonal antibody. Rabbit anti-goat IgG, then anti-AZTMP goat polyclonal is coated to the solid phase.

The sample incubated for about 40 minutes and then 100 µl of tracer, an AZTMP analogue conjugated to an isoluminol derivative is added. During the first incubation, AZTMP binds to the solid phase. In the second incubation, the tracer conjugate competes for binding with the AZTMP in the solution. After a 20 minute incubation, the unbound material is removed with a wash cycle. The starter reagents are then added and a flash chemiluminescent reaction is initiated. The light signal is measured by a photomultiplier as relative light units (RLU) and is proportional to the concentration of TK present in calibrators, controls, or samples.

Figure 3:
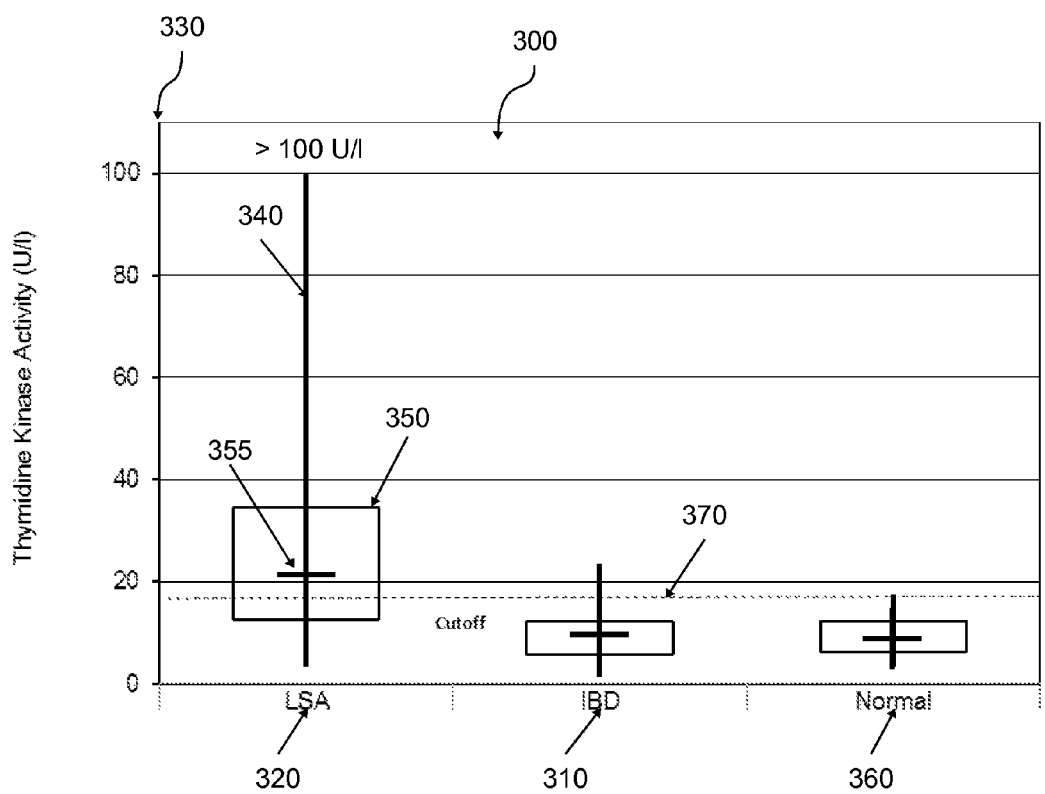
FIG. 3 is a plot of the results of measuring thymidine kinase in three groups of cats, one group affected by lymphoma, the second group affected by inflammatory bowel disease, and the third group that is unaffected by either inflammatory bowel disease or lymphoma, in accordance with the teachings of the invention.

FIG. 3 is a plot of the results of measuring thymidine kinase in three groups of cats, one group affected by lymphoma, the second group affected by inflammatory bowel disease, and the third group that is unaffected by either inflammatory bowel disease or lymphoma, in accordance with the teachings of the invention. Plot 300 shows the data plots for a group affect by lymphoma 320, a group affected with IBD 310, and a group unaffected by either lymphoma or inflammatory bowel disease 360. The third group is considered to show normal levels of TK activity, hence the third group is labeled as "Normal". The ordinate axis 330 shows the enzymatic activity of TK in Units per liter. The vertical bars (e.g., bar 340) respectively represent the spread between the maximum and the minimum values of measured activities for each group. For each group, a box (e.g., box 350) represents the level of measured TK activity respectively corresponding to the first quartile of the group, represented by the bottom of the box, and the third quartile of the group represented by the top of the box. The width of each box represents no statistical data.

The dash line 370 graphically represents 15.5 U/l cutoff value determined to be an indicator above which an animal may be suspected of having LSA. In some cases, the measured TK activity level may for a given subject exceed a predetermined maximum level. For example, given a maximum value (e.g., 100 U/l) of the range of sensitivity of a given method for measuring TK activity, a measurement of TK level would only show 100 U/l even as the true value may be much higher than 100 U/l. In the method provided by the invention the latter inaccuracy is not a concern, since a higher than the cutoff level is already indicative of a high probability that the subject under test has LSA.

TABLE 1

Test Results from three (3) groups.

| | LSA | IBD | Normal |
|---|---|---|---|
| Third Quartile | 34.5 | 12.3 | 12.2 |
| Maximum | >100 | 23.5 | 17.4 |

TABLE 1-continued

Test Results from three (3) groups.

|  | LSA | IBD | Normal |
|---|---|---|---|
| Median | 21.2 | 9.5 | 8.7 |
| Minimum | 3.2 | 1.2 | 3.2 |
| First Quartile | 12.4 | 5.7 | 6.3 |

Table 1 provides statistical data obtained from a proof of concept test on three (3) groups as described above. The data show a median value of 21.2 U/l for the group histologically determined to have lymphoma, which is significantly higher than the median value of either the group affected by inflammatory bowel disease or the normal group. The statistical data of Table 1 are used to plot graph 300 of FIG. 3.

FIG. 3 and Table 1 illustrate the significant difference of TK activity between the lymphoma-affected group on one hand, and the IBD-affected group or the normal group on the other hand. A cutoff of segregation between the two groups according to the above test may be established around 15.5 Units per liter of enzymatic activity. An cat showing activity levels of TK higher than 15.5 U/l has a high probability of having lymphoma.

Figure 4:
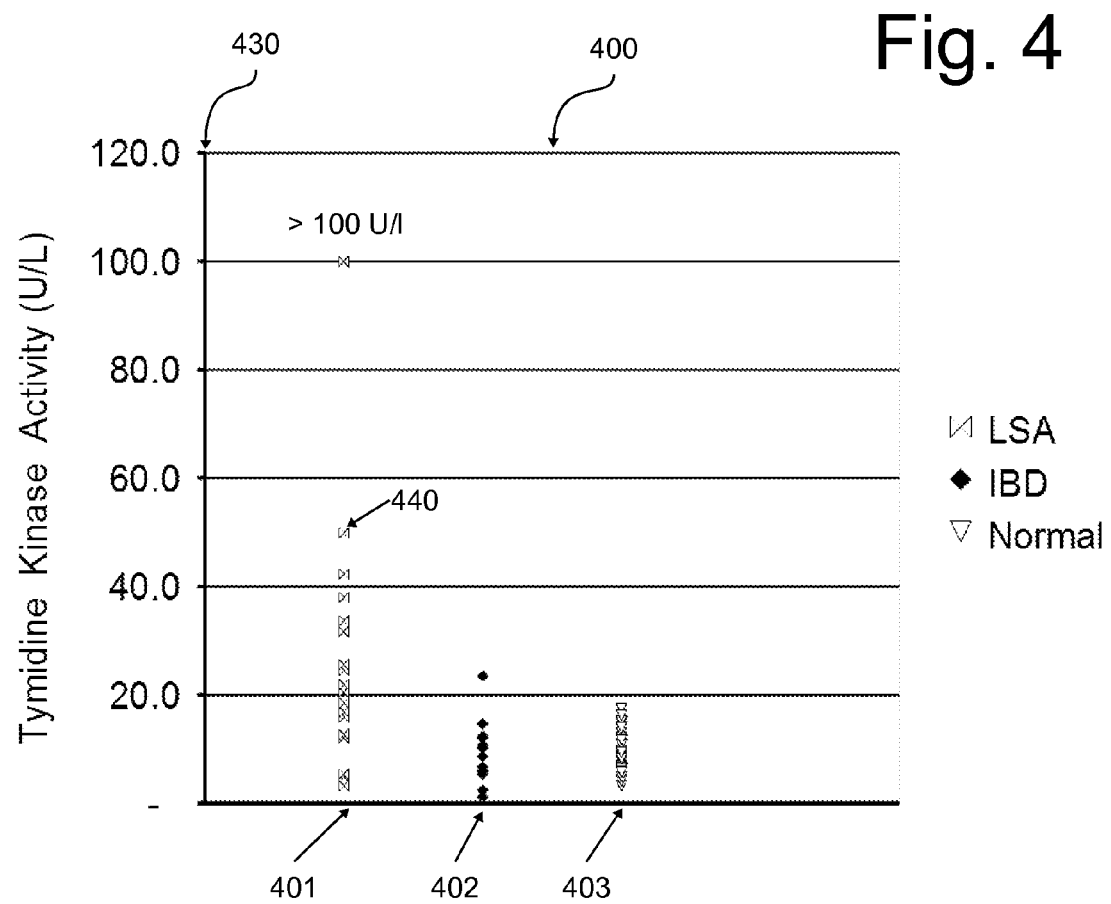
FIG. 4 is a scatter plot of individual measurements obtained from a test study conducted in accordance with the teachings of the invention.

FIG. 4 is a scatter plot of individual measurements obtained from a test study conducted in accordance with the teachings of the invention. Plot 400 represent measurement data obtained from three (3) groups (as described above), wherein one group 401 comprises cats that have been shown using a histological test to lymphoma, a second group 402 comprises cats that have been shown to have inflammatory bowel disease, and third group 403, the normal group. The ordinate axis 430 represents TK activity level in Units per liter. Each data point 440 represents a separate subject, the measurement 440 may represent a single TK measurement or an average of more than one test from the same cat.

Thus, a method a system that allow a practitioner to detect a level of enzymatic activity of thymidine kinase in the blood of a cat, and determine a probability of presence of lymphoma in order to guide further diagnoses of the disease.

The claimed invention is:

1. A method for diagnosing lymphoma in cats comprising the steps of:
   obtaining a quantity of blood from a cat;
   obtaining a portion of said quantity of blood containing thymidine kinase;
   measuring in said portion an activity of thymidine kinase; and
   determining a high probability for said cat to have lymphoma if said amount of thymidine kinase is present at an activity level of at least 15.5 units per liter.

2. The method of claim 1, wherein said step of measuring further comprising mixing said portion with a mixture of a substrate having 3'-derivative of thymidine, a phosphate donor and a buffer system.

3. The method of claim 2, wherein said step of measuring further comprising:
   obtaining a phosphorylated product derived from said substrate;
   attaching a magnetized marker to said phosphorylated product;
   applying a magnetic field to retain said phosphorylated product;
   washing said phosphorylated product; and
   measuring the luminescence of said product.

4. The method of claim 2 further comprising using a nucleoside triphosphate for providing said phosphate donor.

5. The method of claim 1, wherein said step of obtaining said portion further comprising obtaining a serum portion of said quantity of blood of at least 150 micro-liter.

6. The method of claim 1, wherein said step of obtaining said portion further comprising obtaining a portion of blood that contains all TK isoenzymes.

7. The method of claim 1 further comprising determining a low probability for said cat to have lymphoma if said thymidine kinase is present at an activity levels below 15.5 units per liter.

8. A method of interpreting whether clinical symptoms in cats indicate a presence of lymphosarcoma comprising:
   obtaining from a cat a set of symptoms comprising at least one of a loss of appetite, a weight loss, a vomiting and a diarrhea;
   obtaining at least one blood sample from said cat;
   measuring an activity level of thymidine kinase in said at least one blood sample;
   determining whether said activity level is greater than about 15.5 Units per liter; and
   segregating said cat showing any of said set of symptoms as being affected by lymphoma, if said activity level is above about 15.5 Units per liter.

9. The method of claim 8, wherein said step of segregating further comprises segregating said cat as being affected by an inflammatory bowel disease, if said activity level is below 15.5 Units per liter.

* * * * *